(12) United States Patent
Guala

(10) Patent No.: US 7,625,359 B2
(45) Date of Patent: Dec. 1, 2009

(54) DEVICE FOR ADMINISTERING MEDICAL LIQUIDS AND METHOD FOR THE MANUFACTURING THEREOF

(75) Inventor: Gianni Guala, Turin (IT)

(73) Assignee: Industrie Borla S.p.A., Moncalieri (Turin) (IT)

( * ) Notice: Subject to any disclaimer, the term of this patent is extended or adjusted under 35 U.S.C. 154(b) by 494 days.

(21) Appl. No.: 11/410,795

(22) Filed: Apr. 25, 2006

(65) Prior Publication Data
US 2008/0009809 A1 Jan. 10, 2008

(30) Foreign Application Priority Data
Apr. 26, 2005 (IT) .......................... TO2005A0276

(51) Int. Cl.
*A61M 5/00* (2006.01)
(52) U.S. Cl. .................................................. 604/246
(58) Field of Classification Search ............ 604/39, 604/246, 288.01–288.03, 523, 533
See application file for complete search history.

(56) References Cited

U.S. PATENT DOCUMENTS

| 4,665,959 A | 5/1987 | Takagi ................... 141/330 |
| 5,222,948 A * | 6/1993 | Austin et al. ................. 604/213 |
| 6,390,130 B1 * | 5/2002 | Guala ........................ 137/859 |
| 2003/0192791 A1 * | 10/2003 | Eek et al. .................... 206/222 |
| 2004/0254537 A1 * | 12/2004 | Conlon et al. ............... 604/175 |

FOREIGN PATENT DOCUMENTS

| GB | 1175428 | 12/1969 |
| WO | WO 83/02245 | 7/1983 |

OTHER PUBLICATIONS

European Search Report for EP 06 11 1809.7—2308, dated Aug. 28, 2006.

* cited by examiner

*Primary Examiner*—Nicholas D Lucchesi
*Assistant Examiner*—Rebecca E Eisenberg
(74) *Attorney, Agent, or Firm*—Heslin Rothenberg Farley & Mesiti P.C.; Victor A. Cardona, Esq.

(57) ABSTRACT

A device for administering medical liquids comprising a tubular element made of moulded plastic material and an elastic sealing body made of elastic thermoplastic material overmoulded within one end of the tubular element with a part for anchorage on the outside of said end.

6 Claims, 5 Drawing Sheets

US 7,625,359 B2

DEVICE FOR ADMINISTERING MEDICAL LIQUIDS AND METHOD FOR THE MANUFACTURING THEREOF

CROSS-REFERENCE TO RELATED APPLICATIONS

This application claims priority from Italian Patent Application No. TO2005A000276, filed Apr. 26, 2005, the entire disclosure of which is incorporated herein by reference.

FIELD OF THE INVENTION

The present invention relates to a device for administering medical liquids, of the type comprising a tubular element and an elastic sealing body, which is applied to one end of the tubular element and can be perforated by a needle or cannula.

Said devices are for example applied to sacs containing medical liquids for intravenous infusion to provide a so-called "injection site" for administering the liquid.

STATE OF THE PRIOR ART

Traditionally, the elastic sealing body consists of an element made of elastomeric material having a conformation such as to enable it to be inserted within the end of the tubular element and blocked there following upon radial deformation of the free edge of said end inwards, or else via an annular retention element constituted, for example, by an annular cap fixed to the tubular element.

A device for administering medical liquids of the above sort according to the art is described and illustrated, for example, in the document No. WO-83/02245.

The above known solution entails various drawbacks. In the first place, the methodology of production requires a series of successive operations that are relatively complex and hence burdensome. First of all, the tubular element and the elastic sealing body are provided separately, then the sealing body is introduced into the end of the tubular element, and finally the edge of said end is deformed radially so as to block the sealing body. In the second place, blocking of the elastic body cannot be guaranteed with the necessary degree of safety should for any reason the operation of plastic deformation of the end edge of the tubular element bring about some fault. Finally, also perfect hermetic sealing of the elastic body against the inner surface of the end of the tubular element cannot be free from defects that could jeopardize perfect fluid tightness, which is unacceptable in view of the delicate and critical purpose for which the device is used.

SUMMARY OF THE INVENTION

The object of the present invention is to overcome the aforesaid drawbacks, and more in particular to provide a device for administering medical liquids of the type defined at the start, which on the one hand can be manufactured in a way that is simpler and more economically advantageous, and on the other is designed to guarantee a more effective and, above all, more secure hermetic closing of the end of the tubular element by the elastic body.

According to the invention, the above objects are achieved by the fact that the elastic sealing body is made of an elastic thermoplastic material and is overmoulded within said end of the tubular element, with a part for anchorage on the outside of said end.

According to a preferred embodiment of the invention, the end of the tubular element is radially widened, and the overmoulded sealing body adheres annularly on the inside and on the outside of said widened end.

Said radially widened end conveniently presents a series of axial projections extending through the overmoulded sealing body.

BRIEF DESCRIPTION OF THE DRAWINGS

The invention, the subject of which is also a method for the fabrication of the device for administering medical liquids, will now be described in detail with reference to the annexed plate of drawings, which are provided purely by of way of non-limiting example and in which.

DETAILED DESCRIPTION OF THE INVENTION

Figure 1:
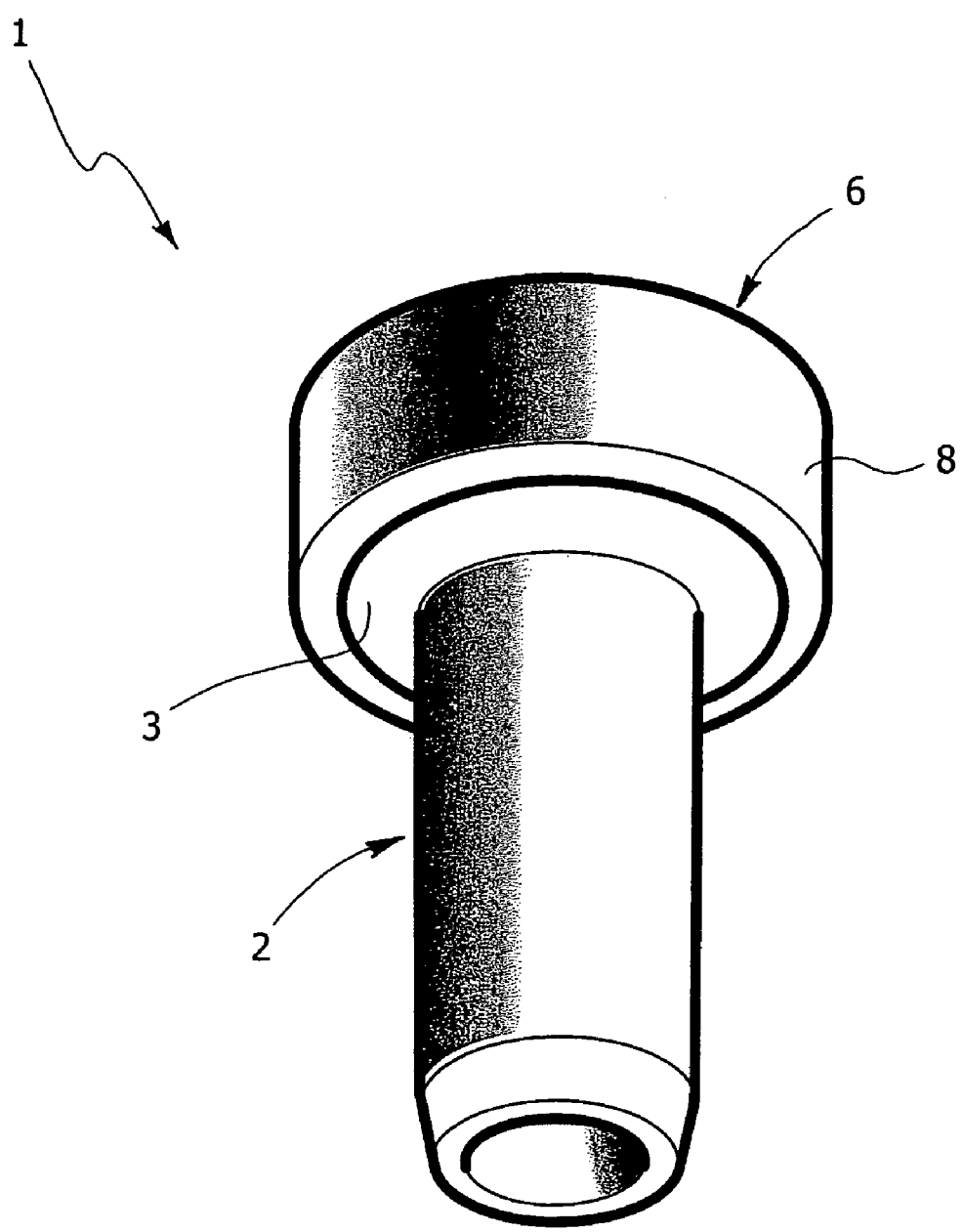
FIG. 1 is a schematic perspective view from beneath of a device for administering medical liquids according to the invention.

With reference to the plate of drawings, number 1 designates as a whole a device according to the invention for administering medical liquids, otherwise referred to as "injection site".

The device 1 is constituted by a tubular element 2 made of moulded thermoplastic material having a radially widened end 3 formed at the top with series (in the example illustrated three in number) of axial projections 5.

Figure 3:
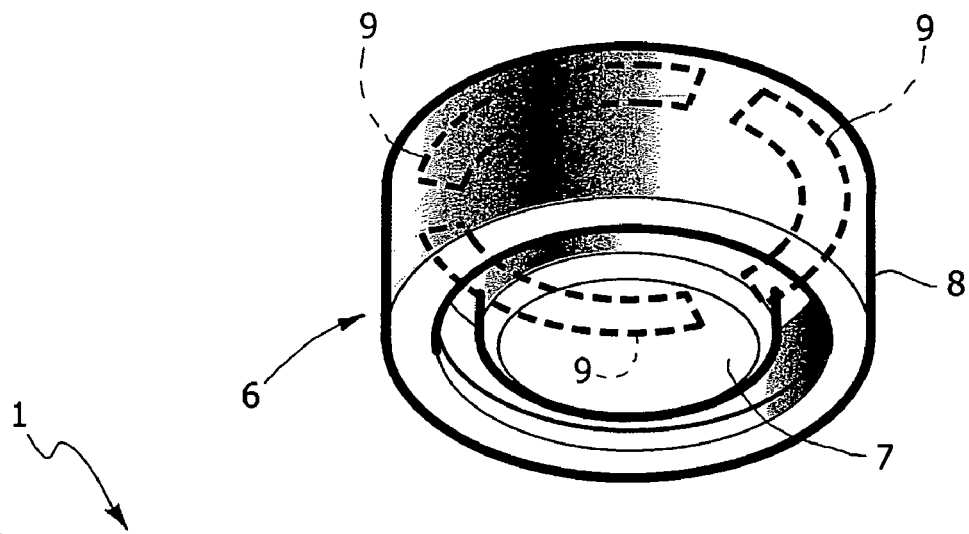
FIG. 3 is an exploded view of the device of FIG. 1.
Figure 3:
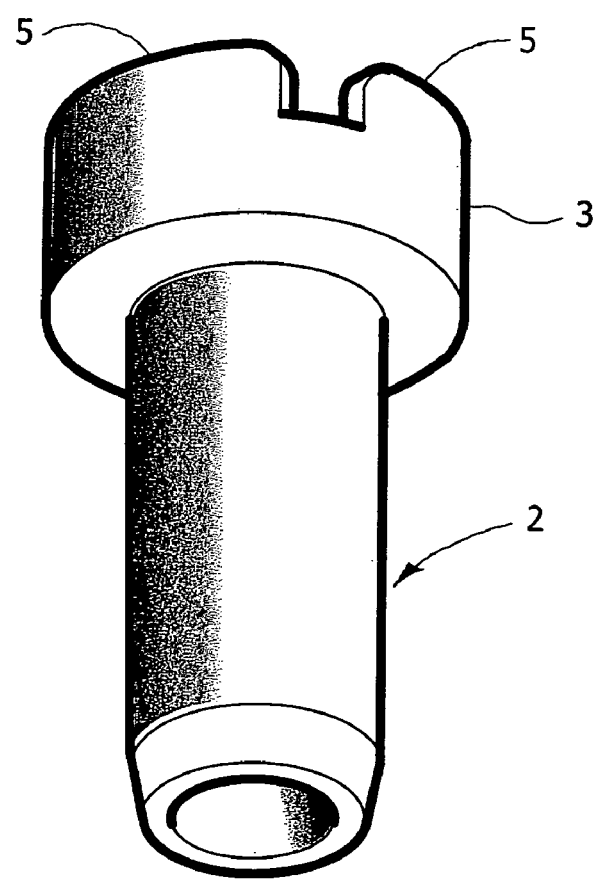
Figure 4:
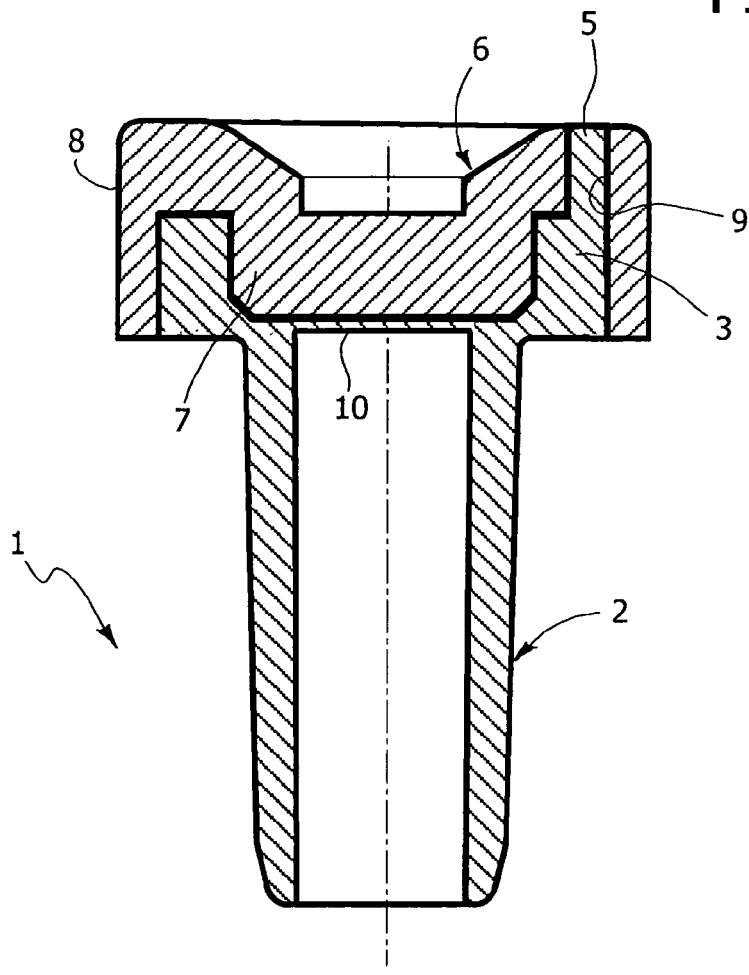
FIG. 4 is an axial sectional view of the device for administering medical liquids.
Figure 5:
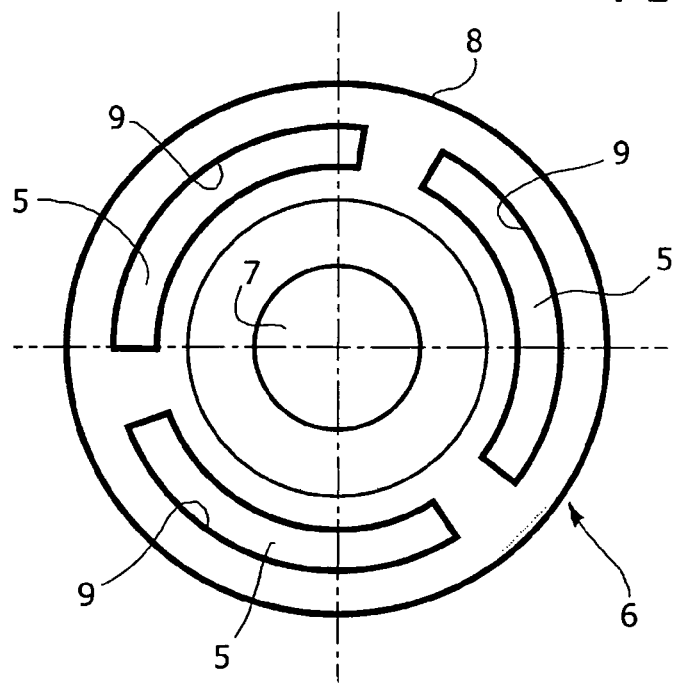
FIG. 5 is a top plan view of the device of FIG. 3.

The reference number 6 designates an elastic sealing body made, according to the invention, of an elastic thermoplastic material (TPE). Once again according to the invention, the sealing body 6 is fixed to the end 3 of the tubular element 2 by overmoulding. In other words, following upon forming by injection moulding of the tubular element 3, the elastic thermoplastic material designed to form the elastic sealing body 6 is injected into the mould, so as to anchor and adhere by physico-chemical adhesion both inside and outside said end 3, in the way highlighted in FIG. 3.

Figure 2:
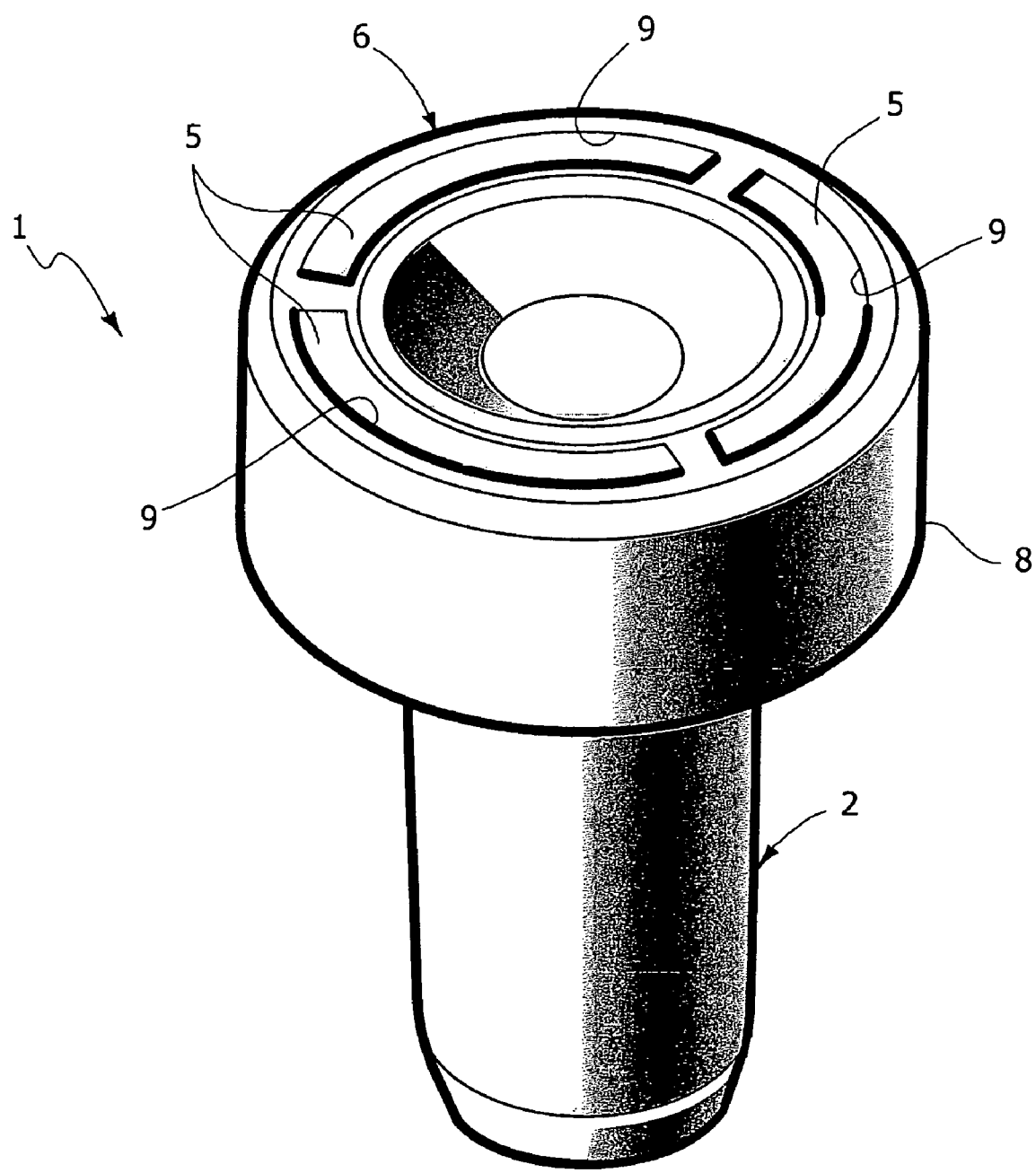
FIG. 2 is a schematic perspective view from above of the device for administering medical liquids.

It should be pointed out that the exploded representation of FIG. 2 corresponds in effect to an other than real situation, since the elastic sealing body 6 does not exist as such, i.e., separate from the tubular element 2, but—as explained previously—it is directly moulded on the end 3 and hence directly integrated with the tubular element 2.

Following upon overmoulding, the elastic sealing body 6 is then arranged astride of the end 3 of the tubular element 2, with a central portion 7 that obstructs in a fluid-tight way said end 3 and a peripheral annular cladding or anchoring member 8, the inner surface of which adheres to the outer surface of the end 3. The axial projections 5 extend through the elastic sealing body 6 and terminate within corresponding openings 9 of said body 6.

One or more of the axial projections can be used for a code identification of the device for administering medical liquids, for example via a particular colouring of its free end visible through the corresponding opening 9.

It is clearly evident that the physico-chemical adhesion resulting from overmoulding of the elastic sealing body 6 on the end 3 of the tubular element 2 guarantees a total and perfect cohesion thereof both on the inside and on the outside of said end 3, thus ensuring a more than secure and reliable hermetic sealing of the tubular element 2. These results are obtained also with an appreciable simplification of the process of production of the device for administering medical liquids 1, in practice halving the steps of production as compared to the conventional devices described in the preamble of the present description.

A further advantage deriving from the conformation of the device for administering medical liquids according to the invention lies in the possibility of easy sterilization thereof, also using steam.

The device 1 is typically designed to be incorporated in a sac for administering medical liquids. Should it be necessary to prevent contact of the liquid contained in the sac with the elastic sealing body 6, a thin transverse diaphragm 10 may be integrally formed within the tubular element 2, upon moulding thereof, in a position immediately adjacent to the central part 7 of the elastic body 6.

The use of the device for administering medical liquids 1 according to the invention does not differ from that of known devices for administering medical liquids. To enable passage of flow from the tubular element 2 outwards, the central part 7 of the elastic body 6 will be simply perforated and traversed by a needle or cannula.

Figure 6:
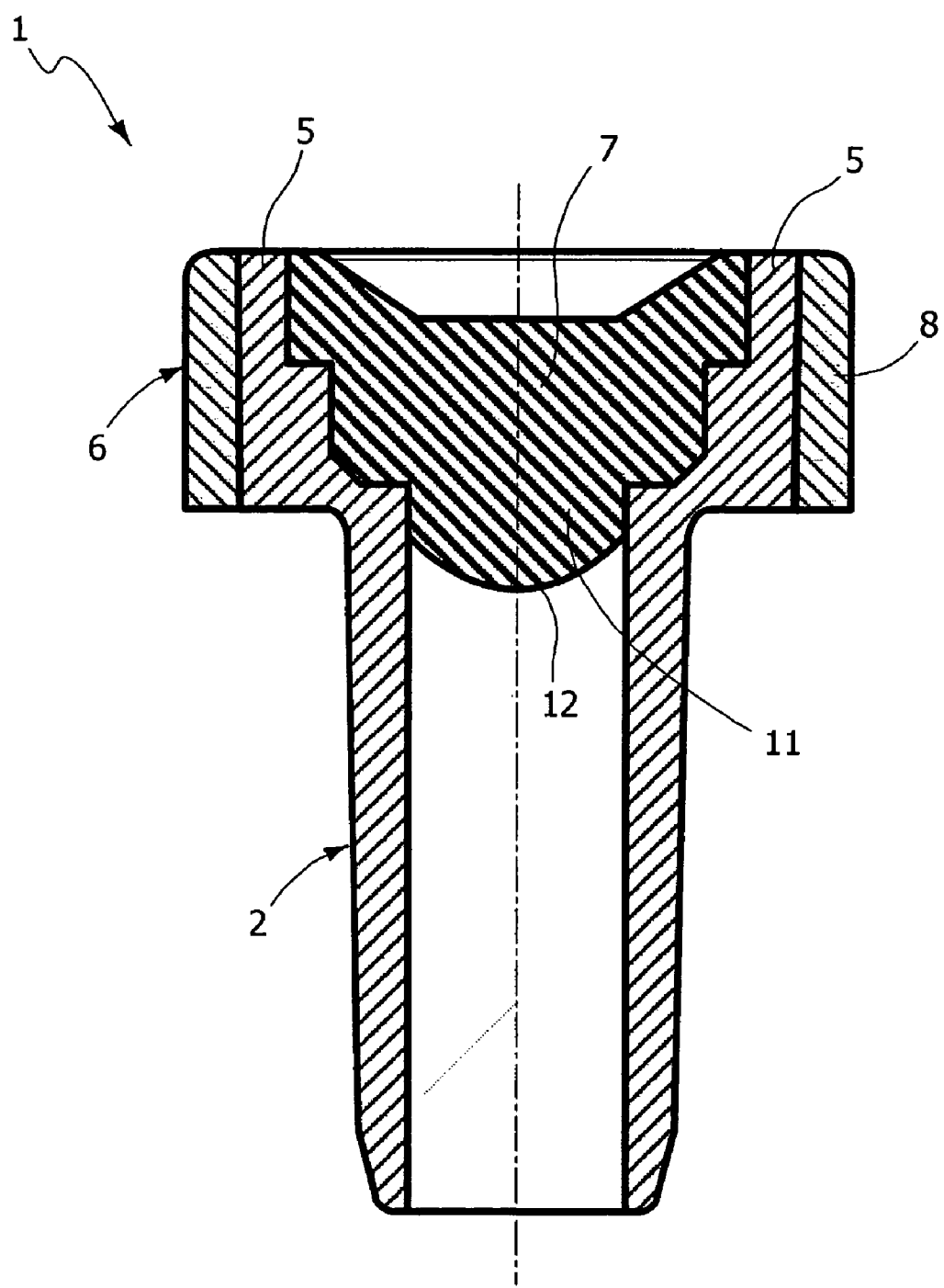
FIG. 6 shows a variant of the device of FIG. 4.

The variant illustrated in FIG. 6 is generally similar to the embodiment described previously, and only the differences will be described in detail using the same reference numbers for the parts that are identical or similar.

In said variant, the elastic sealing body 6 overmoulded on the end 3 of the tubular element 2 has a thickened internal axial portion 11, which projects axially within said tubular element 3 and the end surface 12 of which has a convex, typically spherical, configuration. Thanks to said configuration, in use, when the needle (or cannula) inserted through the elastic sealing body 6 is extracted and removed from the device, the possible pressure of fluid within the tubular element 2 provides a ready and complete hermetic seal of the corresponding hole made through the elastic sealing body 6. This effect is due to the radial components of said pressure acting on the convex surface 12 of the portion 11.

Of course, the details of construction and the embodiments may vary widely as compared to what is described and illustrated herein, without thereby departing from the scope of the present invention, as defined in the ensuing claims.

What is claimed is:

1. A device for administering medical liquids, comprising:
    a tubular element made of moulded plastic material and an elastic sealing body, which is applied in a fluid-tight way at one end of the tubular element and can be perforated by a needle or cannula, wherein said sealing body is made of an elastic thermoplastic material and is overmoulded within said end of the tubular element, with a part for anchorage on the outside of said end;
    wherein said end of the tubular element has a series of axial projections extending through said overmoulded sealing body;
    the elastic body arranged astride of the end of the tubular element and astride of each axial projection of said series of axial projections; and
    the axial projections having free ends exposed to the outside of the device through openings of the body, said free ends usable for code identification.

2. The device according to claim 1, wherein said end of the tubular element is radially widened and said overmoulded sealing body adheres annularly on the inside and on the outside of said widened end.

3. The device according to claim 1, wherein said overmoulded sealing body has an internal axial portion projecting within said tubular element and having an end surface with a convex configuration.

4. A method for the fabrication of a device for administering medical liquids comprising:
    forming a tubular element of moulded plastic material
    applying an elastic sealing body at one end of the tubular element, the sealing body configured to be perforated by a needle, wherein said sealing body comprises an elastic thermoplastic material;
    overmoulding said sealing body within said end of the tubular element so as to form a part of anchorage on the outside of said end;
    forming said end of the tubular element with a series of axial projections and traversing said sealing body by said series of axial projections following upon overmoulding thereof on said end of the tubular element;
    arranging the elastic body astride of the end of the tubular element and astride of each axial projection of the series of axial projections; and
    the axial projections having free ends exposed to the outside of the device through openings of the body, the free ends usable for code identification.

5. The method according to claim 4, further comprising forming said end of the tubular element with a radially widened configuration and overmoulding said sealing body so as to adhere annularly on the inside and on the outside of said widened end.

6. The method according to claim 4, further comprising forming said overmoulded sealing body with an internal axial portion projecting within said tubular element and having one end surface with a convex configuration.

\* \* \* \* \*